United States Patent [19]

Fjellström

[11] Patent Number: 5,614,221
[45] Date of Patent: Mar. 25, 1997

[54] METHOD OF PREPARING A DRUG DELIVERY SYSTEM COMPRISING A DRUG AND A GEL USING A SYRINGE

[75] Inventor: Torsten Fjellström, Uppsala, Sweden

[73] Assignee: Medivent, Uppsala, Sweden

[21] Appl. No.: 344,707

[22] Filed: Nov. 21, 1994

Related U.S. Application Data

[63] Continuation of Ser. No. 848,958, filed as PCT/SE90/00683, Oct. 22, 1990.

[30] Foreign Application Priority Data

Oct. 23, 1989 [SE] Sweden ................... 8903503

[51] Int. Cl.⁶ .................. A61K 9/10; A61K 47/36
[52] U.S. Cl. ........................ 424/488; 424/423
[58] Field of Search .................. 424/488, 489, 424/486, 499–501, 422–23, 426, 428, 462, 484, 487, 497

[56] References Cited

U.S. PATENT DOCUMENTS

Re. 29,066 12/1976 Evans ..................... 429/499
4,169,804 10/1979 Yapel ..................... 424/488
4,474,752 10/1984 Haslam et al. ............. 424/78
4,624,665 11/1986 Nuwayser ................. 424/449

FOREIGN PATENT DOCUMENTS 0140255 10/1984 European Pat. Off. .
0224987 8/1986 European Pat. Off. .
0221505 10/1986 European Pat. Off. .
3626868 2/1988 Germany .
063624 3/1988 Japan .

*Primary Examiner*—Edward J. Webman
*Attorney, Agent, or Firm*—Browdy and Neimark

[57] ABSTRACT

This invention relates to a drug delivery system comprising one or more pharmacologically active substances, aggregating agent and a polysaccharide matrix having pseudoplastic properties, to a method for preparing the same, and to the use thereof for providing slow release of the active substance(s) in a biocompatible environment following in vivo injection thereof. The method enables combining of the active substances and the matrix without prior suspending or dissolving the former in an aqueous media. The drug delivery system allows injection of aggregated drugs giving prolonged drug release in a biocompatible environment.

7 Claims, 1 Drawing Sheet

METHOD OF PREPARING A DRUG DELIVERY SYSTEM COMPRISING A DRUG AND A GEL USING A SYRINGE

This application is a continuation of application Ser. No. 07/848,958, filed Apr. 23, 1992.

The present invention relates to a drug delivery system comprising one or more pharmacologically active substances and a polysaccharide matrix having pseudoplastic properties, to a method for preparing the same, and to a method for the use thereof for providing slow release of the drug in a biocompatible environment following in vivo injection.

Parenteral drug administration by injection is readily achieved with water soluble drugs dissolving easily in the diluent, in most cases physiological saline. However, in performing injection of non-soluble drugs the drug particles tend to occlude the hypodermic needle not only making the injection thereof difficult but also causing a loss of the drug and, thereby, an inexactly administered dose. Injection of slowly dissolving drugs requires, in addition to the above drawbacks of the non-soluble drugs, a considerable amount of time for preparing the solution to be injected. Pre-prepared injectable drugs are subject to substantial activity losses and, therefore, it is desired to keep the drug and diluent apart prior to use.

To achieve a slow release or depot action of a drug in vivo it is known to aggregate the drug, for example with a polylactide aggregate. This aggregate is implanted in a desired position within the human or animal body or injected. An example of this is aggregated contraceptive drugs implanted subcutaneously, for example in the form of a so called contraceptive-rod for prolonged use. These depot preparations are extremely desirable since they give a low dosage uniformly spread throughout the day and night, and are also suitable for individuals with a bad memory and for animals. The known drug aggregates cannot be injected into a desired site of the human or animal body and remain there until the drug delivery is completed. The solution to this problem has hitherto been implantation of larger drug aggregates, such as the above mentioned contraceptive-rod, but these are not biocompatible and, therefore, cause irritation of adjacent tissue and sometimes have to be removed surgically.

The properties of glucoseamine glucans, for example hyaluronic acid and its derivatives, have been known for a long time. The biocompatibility and lack of immunological response in vivo are the main properties rendering these useful agents within the medical field. The most known use of hyaluronic acid is for ophtalmic surgery. Also, a known use thereof is as a carrier for water-soluble drugs, see for example U.S. application Ser. No. 804,178, which corresponds to EP 224,987.

EP 224 987 describes a combination of a pharmacologically active substance and a pseudoplastic gel as being biocompatible and injectable. However, the active substance is not aggregated and, therefore, the combination does not give a depot or slow release action of the drug in vivo following injection thereof. Furthermore, the methods of preparing the combination involves dissolving or diluting the drugs in aqueous solution which is time consuming and only enables use of water-soluble drugs because water-insoluble drugs precipitate in the aqueous solution.

U.S. Pat. No. 4,795,741 describes a pseudoplastic gel combination intended for therapeutic percutaneous embolization of, for example, aneurysms, and comprising, in addition to the pseudoplastic gel, thrombin, and optionally: metal powder, Ba-salt, low molecular weight drug. It does not contain an aggregated drug and, therefore, a prolonged depot action of the drug is neither intended nor achieved.

An object of the present invention is to enable readily preparation and injection of a drug delivery system comprising a water insoluble or poorly soluble drug and a fluent pseudoplastic gel without the above drawbacks associated with prior art, ie without precipitation, clogging, and loss of drug material. Another object of the invention is to provide injectable and biocompatible depot preparations.

These objects are achieved with a drug delivery system comprising one or more pharmacologically active substances and a polysaccharide matrix having pseudoplastic properties, and with a method of parental injection.

Figure 1:
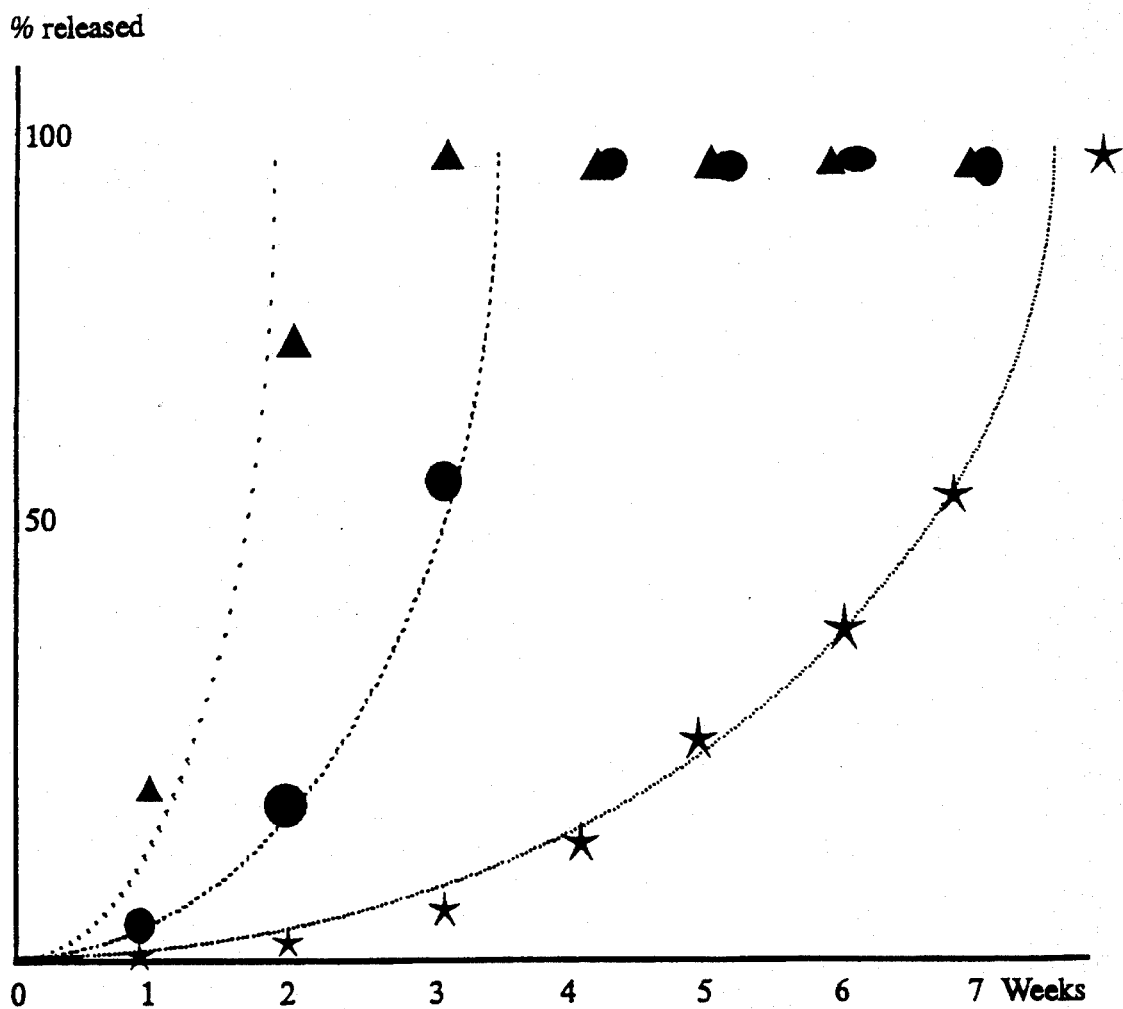
FIG. 1 shows typical drug release rates according to the invention.
Figure 1:
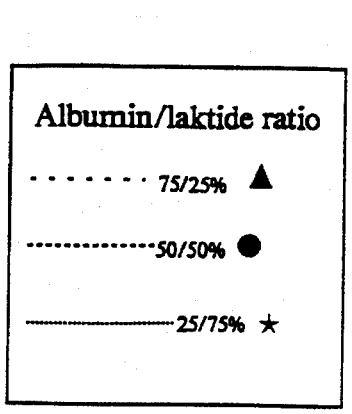

The present invention takes advantage of the pseudoplastic properties of, for example, hyaluronic acid having a shearing dependent viscosity. By performning repeated experiments, we surprisingly found that water insoluble or slowly soluble drugs, for example particulate, crystalline and freeze dried drugs, not possible to inject in water or physiological spline without the above mentioned drawbacks, readily can be prepared and injected in association with pseudoplastic solutions.

According to the method of the invention, one or more water insoluble or poorly soluble drugs is first brought together with the pseudoplastic gel vehicle in a vial. Thereafter, the combination is caused to flow by being aspirated into a syringe provided with a cannula, the syringe contents are injected back to the vial and the aspirating procedure is repeated, under visual observation, until substantially all of the drug particles are incorporated into the pseudoplastic gel. Now, the combination is ready for injection. For storing purposes, the drug is suitably kept in one vial and the pseudoplastic gel in another vial, preferably a syringe. At the time of use, the gel is pushed out of the syringe into the drug vial and thereafter the combination is drawn back into the syringe, the drug being mixed with the gel substantially during the low viscosity phase of the gel, i.e. when it passes through the cannula. The method of the invention allows injection of water insoluble or poorly soluble drugs without prior suspending or dissolving thereof in aqueous media. This is not only time saving but also eliminates the problems associated with prior art, i.e. precipitation, clogging and loss of valuble drug material.

Alternatively, the pseudoplastic gel may be dehydrated initially and rehydrated together with the drug particles prior to use, capturing the drug within the pseudoplastic gel.

In the present invention, there is used a polysaccharide matrix with pseudoplastic properties as a vehicle of one or more pharmacologically active substances. The pseudoplastic gel comprises water and 0.05 to 20% w/w polysaccharide matrix and examples thereof include glucoseamine glucans, hydroxy ethylcellulose, carboxy methyl cellulose or xanthan gum. The preferred matrix is glucose amine glycan providing an excellent biocompatibility eliminating irritation of adjacent tissue when administred in vivo.

Examples of drugs which may be used in association with the invention are hormones, growth factors, enzymes, antibiotics and combinations thereof.

Also, the novel method of preparing the drug delivery system according to the invention enables incorporation of aggregated drug particles into the pseudoplastic gel to obtain a slow release action. Thus, it is now possible according to the present invention to inject aggregated drugs to a desired site in the human or animal body and, at the same time, give these drugs a biocompatible protection in vivo. For example, the active drugs can be aggregated by solvent evaporation prior to combining with the pseudoplastic gel. The upper limit of the drug particle diameter has been determined to be about 1000 μm and this means that large as well as small drug particles can be aggregated and then incorporated into the gel. Drug substances which are very active require a smaller amount than less active ones. Optionally, the small drug particles can be aggregated with several layers, and thereby delay the drug release further, provided the diameter is less than about 1000 μm. Of course, this can be done in a controlled fashion enabling the design of drug delivery systems with one or more drugs having desired release rates. According to the invention it is thus possible to incorporate aggregated, for example polylactide-aggregated, drugs in the pseudoplastic gel to achieve a depot action of the drug in vivo. The preferred amount of polylactide is from about 25 to about 99% (w/w). By aggregating the drugs in varying degrees, release rates within desired ranges can be obtained. Thus, it is possible to aggregate the pharmacologically active substances to the same extent to provide a uniformly controlled drug delivery rate. Alternatively, the pharmacologically active substances are aggregated to a different extent to provide differently controlled drug delivery rates and, thereby, a wider drug delivery range. Also, the drug delivery system may comprise non-aggregated active substance(s) so that drug delivery will start without delay.

As appreciated from the above, water insoluble as well as water-soluble drugs can be given a slow release rate in vivo by aggregating and incorporating thereof in a pseudoplastic gel according to the method of the invention.

The following Examples are intended to illustrate the invention further without limiting the scope thereof.

EXAMPLE 1

This example shows typical drug release rates of a drug delivery system according to the present invention. High molecular weight d,l poly lactide was used to encapsulate albumin. The method of preparation was solvent evaporation which, optionally, was performed repeatedly to obtain larger beads of polylactide aggregated albumin. Thereafter, the pseudoplastic combination was prepared as described above and the different combinations were injected into test tubes containing physiological saline.

The results are shown in FIG. 1, wherein the ▲—▲ curve represents an albumin/lactide ratio of 75/25 w/w %, the ●—● represents an albumin/lactide ratio of 50/50 w/w %, and the ★—★ curve represents an albumin/lactide ratio of 25/75 w/w %.

From FIG. 1 it appears that the higher the polylactide content, the longer duration of the drug delivery. The largest beads, represented by ★—★ in FIG. 1 are about 200 μm in diameter and have their maximum release after about 7 weeks. The least aggregated particles, represented by ▲—▲ in the FIGURE are about 15 μm in diameter and have their maximum release after about 1 to 2 weeks. The intermediate particles, represented by ●—● in the FIGURE are only illustrative and it should be understood that any size in between the two outermost curves are obtainable. The 200 μm beads are sprayed twice but it is, of course, possible to repeat the spraying more times provided the size does not exceed about 1000 μm being the upper limit for incorporation into the drug delivery system according to the invention. Earlier drug release than the 15 μm particles can be obtained by incorporating non-aggregated forms of the drug into the combination. In FIG. 1, 100% release equals the maximum obtainable.

EXAMPLE 2

This example compares the amount of drug particles (tested compounds: albumin mw 60 000 and lysozyme mw 10 000) aspirated into saline (prior art), and pseudoplastic gel (present invention), respectively.

Drug powder of the tested compounds was put into a syringe from a glass injection vial by injecting a fixed amount of fluid (ie gel or saline) and aspirating the fluid-powder mixture once through a 20 gauge injection needle. The aspirated amount of powder was measured. The results are given in Table 1 below.

TABLE 1

| | % powder aspirated into | |
|---|---|---|
| Powder | saline (prior art) | pseudoplastic gel (present invention) |
| Albumin | 80 | 90 |
| Albumin, lactide aggr. | 20 | 95 |
| Lysozyme | 75 | 95 |
| Lysozyme, lactide aggr. | 25 | 95 |

Most of the losses using saline as the aspirating fluid was due to aggregation in the mixing vial. By allowing over night mixing of the powder and the test fluid the recovery of the albumin and lysozyme was almost 100% whereas the recovery of the polylactide bead preparations did not change.

Accordingly, the present invention allows preparation and injection of water insoluble and poorly soluble drugs in a substantially more rapid and economical way compared to prior art. Furthermore, it allows injection of biocompatible depot preparations having controlled drug delivery rates.

Medical applications possible to perform in view of the basic teachings of the present invention are obvious for a person skilled in the art. As an example, there can be mentioned combination preparations of, for example, streptokinase and heparin aggregated suitably and incorporated in a pseudoplastic gel for administration in the vicinity of the coronary vessels to prevent coronary embolism.

I claim:

1. A method of preparing a drug delivery system for parental injection of water insoluble or semi-soluble active ingredient(s), wherein one or more active ingredient(s) are brought together with a pseudoplastic polysaccharide gel in a vial, the combination is aspirated into a syringe provided with a cannula, the combination is ejected from the syringe into a container, and the aspirating procedure is repeated, under visual observation, until substantially all of the active ingredient(s) is/are incorporated into the pseudoplastic gel.

2. A method according to claim 1, wherein the active ingredient(s) are aggregated with an aggregating agent giving the active ingredient(s) a slow release action in vivo by encapsulation thereof by said aggregating agent, by solvent evaporation prior to combining with the pseudoplastic gel.

3. A method according to claim 2, wherein said aggregating agent is d,l polylactide.

4. A method according to claim 3, wherein said aggregating agent is 25–99% w/w d,l polylactide.

5. A method according to claim 2, wherein the aggregation step is repeated to provide slower drug delivery rates.

6. A method according to claim 2, wherein the aggregation step is performed to the same or to different extents to provide differently controlled drug delivery rates and, thereby, a wider drug delivery range.

7. A method for providing slow release of an active substance in vivo in a biocompatible environment, comprising parentally injecting a drug delivery system made according to claim 1 at a desired site in a human or animal.

* * * * *